(12) United States Patent
Bembridge et al.

(10) Patent No.: US 9,901,745 B2
(45) Date of Patent: Feb. 27, 2018

(54) DEVICE FOR LIGHT THERAPY WITH IMPROVED WEARING COMFORT

(75) Inventors: Mathew Lee Bembridge, Rotterdam (NL); Guofu Zhou, Best (NL); Jorgen Meeusen, Eindhoven (NL); Wouter Petrus Kaandorp, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 680 days.

(21) Appl. No.: 14/127,655

(22) PCT Filed: Jun. 15, 2012

(86) PCT No.: PCT/IB2012/053016
§ 371 (c)(1),
(2), (4) Date: Dec. 19, 2013

(87) PCT Pub. No.: WO2013/001396
PCT Pub. Date: Jan. 3, 2013

(65) Prior Publication Data
US 2014/0128942 A1    May 8, 2014

(30) Foreign Application Priority Data

Jun. 28, 2011  (EP) .................................... 11171641

(51) Int. Cl.
*A61N 5/06*      (2006.01)
(52) U.S. Cl.
CPC .... *A61N 5/0613* (2013.01); *A61N 2005/0645* (2013.01); *A61N 2005/0652* (2013.01); *A61N 2005/0662* (2013.01)

(58) Field of Classification Search
CPC .. A61N 5/0613; A61N 5/0616; A61N 5/0624; A61N 5/0625; A61N 2005/0632;
(Continued)

(56) References Cited

U.S. PATENT DOCUMENTS 5,259,380 A * 11/1993 Mendes ............... A61N 5/0616
606/2
5,358,503 A * 10/1994 Bertwell ............. A61N 5/0616
257/E25.028

(Continued)

FOREIGN PATENT DOCUMENTS

CN       2812717 Y      9/2006
WO    200015296 A1      3/2000
(Continued)

*Primary Examiner* — Ahmed Farah

(57) ABSTRACT

A light-emitting device includes a plurality of light-emitting elements or light sources and a flexible pad for positioning and conforming the light-emitting device to a portion of a body of a user. The flexible pad includes a three-dimensional structure having a plurality of protrusions for contacting a skin of the portion of the body when the light-emitting device is applied to the portion of the body by the flexible pad. Further, the three-dimensional structure includes a plurality of recesses for creating a clearance between the skin and the flexible pad when the light-emitting device is applied to the portion of the body, and a plurality of apertures for engaging with the plurality of light-emitting elements. Each protrusion includes an extended part and a withdrawn part, where the extended part is further extended than the withdrawn part, and the extended part is configured to contact the skin.

19 Claims, 2 Drawing Sheets

(58) Field of Classification Search
CPC .... A61N 2005/0643; A61N 2005/0645; A61N 2005/0652
USPC ............ 607/88–91, 93, 96, 100; 606/9, 13; 604/304–307, 890.1; 128/898
See application file for complete search history.

(56) References Cited

U.S. PATENT DOCUMENTS

| | | | | |
|---|---|---|---|---|
| 5,616,140 | A * | 4/1997 | Prescott | A61N 5/06 606/10 |
| 5,698,866 | A * | 12/1997 | Doiron | A61N 5/062 257/717 |
| 6,096,066 | A * | 8/2000 | Chen | A61N 5/062 607/88 |
| 6,290,713 | B1 * | 9/2001 | Russell | A61N 5/0616 607/88 |
| 6,860,896 | B2 * | 3/2005 | Leber | A61N 5/0619 128/898 |
| 6,955,684 | B2 * | 10/2005 | Savage, Jr. | A61N 5/0618 607/88 |
| 7,147,653 | B2 * | 12/2006 | Williams | A61N 5/0621 607/88 |
| 7,503,927 | B1 * | 3/2009 | Vetanze | A61N 1/0408 607/115 |
| 7,721,349 | B1 * | 5/2010 | Strauss | A41D 13/0053 2/102 |
| 8,048,136 | B2 * | 11/2011 | Chung | A61N 5/0621 607/88 |
| 9,271,875 | B2 * | 3/2016 | Freer | A61F 13/0233 |
| 2005/0182460 | A1 | 8/2005 | Kent | |
| 2007/0277806 | A1 * | 12/2007 | Dodo | A61F 7/034 126/263.02 |
| 2009/0204100 | A1 * | 8/2009 | Van Pieterson | A61B 5/0008 604/503 |
| 2010/0179469 | A1 * | 7/2010 | Hammond | A61N 5/0603 604/20 |
| 2011/0092863 | A1 | 4/2011 | Kim | |
| 2011/0275978 | A1 * | 11/2011 | Hyde | A61K 33/00 604/20 |
| 2013/0030341 | A1 * | 1/2013 | Freer | A61F 13/0233 602/43 |
| 2016/0114186 | A1 * | 4/2016 | Dobrinsky | A61L 2/10 607/94 |

FOREIGN PATENT DOCUMENTS

| | | |
|---|---|---|
| WO | 2007047892 A1 | 4/2007 |
| WO | 2007091549 A1 | 8/2007 |
| WO | 2008144157 A1 | 11/2008 |

* cited by examiner

DEVICE FOR LIGHT THERAPY WITH IMPROVED WEARING COMFORT

CROSS-REFERENCE TO PRIOR APPLICATIONS

This application is the U.S. National Phase application under 35 U.S.C. § 371 of International Application No. PCT/IB2012/053016, filed on Jun. 15, 2012, which claims the benefit of European Patent Application No. 11171641.1, filed on Jun. 28, 2011. These applications are hereby incorporated by reference herein.

FIELD OF THE INVENTION

The present invention generally relates to the field of light-emitting devices. Specifically, the present invention relates to a light-emitting device for light therapy wherein the light-emitting device is intended to be used in close proximity to the skin.

BACKGROUND OF THE INVENTION

A phototherapy device generally comprises a light-emitting device including e.g. one or more light-emitting diodes (LEDs) or a laser for causing a light induced effect e.g. in a skin layer or in a muscle area of a subject that is treated, by illuminating or irradiating the skin with light emitted from the light-emitting device. Effectiveness of such treatment may at least partly depend on the amplitude of the light output or irradiance and of the total dose of light energy applied. For practical and functional reasons, it is often desired that phototherapy devices are wearable on the skin to have a maximum efficiency and also maximum comfort for the user wearing the phototherapy device.

US-20050182460-A1 discloses a light therapy device which is provided with a housing unit and a LED pad. The LED pad comprises a flexible base, an LED array and a back support member. The flexible base includes a plurality of apertures, each aperture dimensioned to receive a single LED therein. The flexible base may be made of a material having elastic yield, and more preferably, is made of a flexible foam. The elastic nature of the base allows the flexible pad to conform to the shape of the treatment area, providing a comfortable fit for the user. Except for the apertures for receiving the LEDs, the upper surface of the LED pad is flat. When this flat surface is brought in contact with the skin, a reduced breathability of the skin becomes a concern and may be a source of irritation of the skin.

WO 2008/144157 A1 discloses a light therapy cap insert for low level light therapy of the hair/scalp, comprising an array of wide-angle emission surface-emitting LEDs combined with a light emitter-scalp separation layer consisting of bristles under laying the LED array in a suitable pattern to maintain adequate separation for the individual LED beams to diverge adequately to achieve uniform illumination. The separation layer includes a plurality of openings oriented relative to the LEDs.

SUMMARY OF THE INVENTION

In view of the above discussion, it would be advantageous to have a light-emitting device having an outer surface for conforming to skin and contacting the skin during use of the device, wherein the outer surface is designed to allow continued breathing or sweating of the skin when the device is attached to the skin. It would also be desirable to maintain a free flow of air between the light-emitting device and the skin when the device is attached to the skin.

To address one or more of these concerns, a light-emitting device in accordance with the independent claim is provided. Preferred embodiments are defined by the dependent claims.

According to a first aspect of the present invention, there is provided a light-emitting device comprising a flexible pad for position and conforming the light-emitting device to a portion of the body, wherein the flexible pad further comprises a three-dimensional structure having a plurality of protrusions for contacting the skin when the light-emitting device is applied to the skin, a plurality of recesses for creating a clearance between the skin and the flexible pad when the light-emitting device is applied to the skin, and a plurality of apertures for engaging with a plurality of light-emitting elements. The protrusions therefore define a skin reference plane which coincides with the skin surface when the light-emitting device is brought in contact with the body portion. The recesses provide an area on the flexible pad that is not contacting the skin when the light-emitting device is applied and therefore allows continued breathing of the skin. The plurality of apertures engage with a plurality of light-emitting elements, preferably one-to-one, such that light emitted from these light-emitting elements is emitted right through the flexible pad in the direction of the skin.

In a further embodiment of the invention, the protrusions are singular features. In the context of this application, singular features are convex individual features. Another way of looking to singular features is by making the comparison with islands arising (protruding) from the sea. Examples of such singular features in the context of this application may be knops, bulging out line segments or arcs, etc. An advantage of the protrusions being singular features is that the recesses surrounding the protrusions create an open structure which allows continuous ventilation between the flexible pad and the skin when the light-emitting device is applied to the skin. The ventilation may be further improved by lining up the plurality of recesses in at least one direction parallel with the skin reference plane of the flexible pad such that the recesses create a preferred low-resistance clearance channel in that particular direction. The recesses may be arranged in a regular pattern so that they line up along more than one direction thereby creating ventilation across the skin in multiple preferred directions.

In another embodiment of the invention, the protrusions correspond to the perimeter of geometric figures wherein singular feature are created by extending some parts of the perimeter further outward (in the direction of protrusion) and withdrawing other parts of the perimeter further inward (in the direction opposite to the protrusion). This type of protrusion may be further referred to as geometric protrusions. The skin reference plane is now defined by the extended parts of the protrusions. The withdrawn parts can be withdrawn to the level of the recesses or can be withdrawn to a level in between the recesses and the extended parts of the protrusions. The surface area of the corresponding geometric figures, i.e. the area within the perimeter, can be fully withdrawn to the level of the recesses or can be withdrawn to a level in between the recesses and the extended parts of the protrusions, e.g. to a level in between the recesses and the withdrawn parts of the protrusion. The surface area of the geometric figures is therefore a recessed area and can be considered part of the plurality of recesses. The withdrawn parts of the protrusions, the recessed surface areas and other recesses create a clearance between the skin reference plane and the flexible pad. In one example, the protrusions may have circular shapes wherein some parts (e.g. some arcs) of the circumference are further extended and other parts (e.g. other arcs) are withdrawn. In another example, the protrusions may have a hexagonal shape wherein the angular points are extended outward and the line segments are withdrawn, or vice versa. Other geometric figures, not restricted to regular figures only, can be used to create protrusions. Moreover, different types of geometric figures may be combined in one flexible pad, for example one area of the flexible pad may be provided with triangular based protrusions whereas another area may be provided with hexagon based protrusions, or they may be mixed. An advantage of using geometric figures as the outline for the protrusions and recesses is that these protrusions and recesses can be arranged in a pattern across the surface of the flexible pad and so improve the dimensional stability of the flexible pad, in a similar way as adding a firm grid to a flexible layer. Dimensional stability is important when flexing and conforming the flexible pad to the skin.

In one embodiment, the protrusions may be arranged in a regular pattern based on a close packing principle of polygons or circles. When using such a pattern also the recesses are arranged according to such a close packing. One of the advantages of the close packing will become clear now when describing the apertures for engaging with or receiving the light-emitting elements. In a preferred embodiment, at locations in the flexible pad where a light-emitting element is to be received, the recessed surface area of the geometric figure comprises or may be replaced by an aperture. The aperture can comprise any three-dimensional shape such as cylindrical, conical, paraboloidal or any other shape that may be optically optimized to direct the emitted light to the skin. The aperture may or may not completely take up the recessed surface area of the protruding geometric figure. The protruding perimeter of the geometric figure may or may not coincide with the outer rim of the aperture. The advantages of a closed packed arrangement of the protrusions now are: (i) it provides good dimensional stability to the outer surface of the flexible pad, (ii) it supports a closed packed arrangement of the light-emitting elements which allows higher optical densities of emitted light at the skin, (iii) it automatically lines up the recesses in multiple directions, i.e. along the symmetry axes of the closed packed pattern, for creating multiple preferred ventilation directions between the flexible pad and the skin, and (iv) a closed packed arrangement is scalable so that dimension stability of the flexible pad, optical density of the light output and ventilation efficiency (breathability and sweat evacuation) can be optimized. Preferred examples of closed packed arrangements are a close packing of circular protrusions and a close packing of hexagonal protrusions.

Other aspects of the inventions involve the height of the protrusions, recesses and apertures of the flexible pad, in a direction perpendicular to the skin reference plane defined by the contact points of the protrusions with the skin. The height difference between the protrusions and the recesses preferably is at least 0.5 mm and more preferable about 1.5 mm, in order to create a practicable clearance space between the recessed areas of the flexible pad and the skin. When using protrusions having an further extended part and a withdrawn part, for example in case of incorporating geometric structures on the surface of the flexible pad, the height difference between the extended parts and the withdrawn part preferably is in the lower range of the range at least 0.5 mm, such as for example about 0.8 mm. The height difference between the extended parts and the recessed surface area of the geometric structure preferably is somewhat larger, such as for example about 1.5 mm. The apertures are 'through-hole' features of which the height (maybe depth would be more suitable) is of course linked to the thickness of the flexible pad and wherein the value is selected based on a preferred distance or clearance between the light-emitting devices and the skin when the light-emitting device at applied to the skin. In the context of this disclosure, 'engaging' of the light-emitting elements with the apertures may refer to aligning the light-emitting elements in front of the apertures without inserting the light-emitting elements in the corresponding aperture or may refer to effectively inserting the light-emitting element partially or entirely in the aperture. The clearance between the light-emitting device and the skin when the light-emitting device is applied to the skin therefore depends not only on the thickness of the flexible pad but also on the way of engaging of the light-emitting elements with the apertures. The height of all these features is a tradeoff between ventilation capability of the flexible pad when the pad is applied to the skin, thickness of the flexible pad which preferably is as low as possible to create maximum ergonomic fit and discreteness during use, and electromechanical or optical consideration with respect to the distance between the light-emitting elements and the skin surface when the light-emitting device is applied to the skin.

Further dimension related aspects of the inventions involve the width of the protrusions, recesses and apertures of the flexible pad, in a direction parallel with the skin reference plane defined by the contact points of the protrusions with the skin. It is suggested to have the width of the protrusions smaller than the width of the recesses, this to allow the clearance channels established by the recesses to be as broad as possible and therewith improve the ventilation capacity of these channels. In a preferred embodiment, the width of the protrusions is less than 50%, preferably less than 20%, most preferably about 10% of the width of the recesses. This ratio does not necessarily apply to the width difference between the extended parts and the withdrawn parts of protrusions, which may have about the same width, but may apply to the width difference between the extended portions of these protrusions and the recessed surface area in between the protrusions. Another dimensional aspect of the invention includes the actual width of the recesses, in a direction parallel with the skin reference plane defined by the contact points of the protrusions with the skin. It is preferred that the width of the recesses or recessed areas is between about 5 mm and about 20 mm, preferably between about 10 mm and about 15 mm. The actual width of the recesses or recessed areas is a tradeoff between ventilation capacity (large recessed areas) and dimensional stability (small recessed areas) in terms of strength to withstand pressure and maintain the clearance when the flexible pad is applied to the skin.

The three-dimension structure of the flexible pad may comprise a woven material, a foam, a silicone material etc. The protrusions, recesses and apertures may be formed by molding, embossing, thermoforming, etc. The flexible pad may also be provided with a thermoformed 3D nanosphere® textile which has the advantage of creating a water repellent and easily cleanable surface e.g. for proper hygiene after use of the light-emitting device at the skin.

In a preferred embodiment the light-emitting device comprises a light-emitting module wherein the light-emitting elements are arranged on and supported by an electronic textile. The light-emitting elements maybe a plurality of blue LEDs wherein the blue LEDs emit light in a wavelength range 430 nm to 460 nm, preferably about 453 nm. These wavelength ranges have shown to be effective for pain relief by providing a soothing warming effect of the superficial skin layers and gently diffusion heat into deeper layers of the skin and muscle structure, and by stimulating the creating and diffusion of NO in the skin and the blood vessels so that blood vessels relax and impurities are more easily removed via the blood flow.

The size of light-emitting module may be smaller than the size of the flexible pad. The flexible pad may then comprise a light-emitting area, alternatively referred to as illumination area, and a blind area, alternatively referred to as dark area. In the light-emitting area of the flexible pad, the three-dimensional structure is provided with protrusions and apertures, whereas in the blind area, the three-dimensional structure is provided with protrusion and recesses. The protrusions in the light-emitting area and the protrusions in the blind area may be of the same type, e.g. based on the same geometric pattern, and the same height. An advantage of using a single pattern of protrusions across the entire surface of the flexible pad is that the dimensional stability, the look and feel, the comfort etc. is experienced as uniform across device. Alternatively, the protrusions in the light-emitting area and the protrusions in the blind area may be of a different type. Advantages of using different patterns or different types of protrusions across the flexible pad may be related to the fact that: (i) breathability or ventilation requirements across the flexible pad may differ between the light-emitting area and the blind area, (ii) a different mechanical stability of apertures (incl. their light-emitting element) in the light-emitting area versus recesses in the blind area may have to be compensated with different protrusion structures, (iii) a close packing of apertures may be required in the light-emitting area for optimal light distribution but a close packing of recesses may not be optimal for ventilation and sweat evacuation in the peripheral area.

In one embodiment the flexible pad comprises a light-emitting area in the center of the pad and a blind area surrounds the center. In a light-emitting device comprising such a flexible pad, the light-emitting module e.g. the light-emitting textile is positioned facing the back of the light-emitting area so that a mapping or engaging of the plurality of light-emitting elements with the plurality of apertures is feasible. Facing the back of the blind area of the flexible pad there may be provided other peripheral or secondary features of the light-emitting device, the primary features being the light-emitting elements, such as connectors, sensors, a user interface, batteries, driver electronics, etc. Advantages of having the peripheral or secondary features of the light-emitting device located in the blind area are (i) that the light-emitting device can be maintained as flat as possible thereby improving flexibility and conformability of the light-emitting device and (ii) that the total size or surface area of the light-emitting device is increased which may benefit comfort e.g. by spreading the skin contact interface across a larger area. In order to provide that additional comfort and dimensional stability, it may therefore be an advantage if the dark area is of a size (surface area) at least half the size (surface area) of the illumination area, preferably about the same size or larger that the illumination area.

In another aspect of the invention, light-emitting devices comprising a flexible pad having features as described in any of the previous paragraphs are used in a wearable, conformable phototherapy device. They may for example be used for the relief of pain using blue light, as explained above. Alternatively or additional red/infrared light-emitting elements may be incorporated for the relief of pain. Red/infrared wavelengths typically penetrate deeper into the skin layers compared to blue wavelengths.

Further objects and advantages of the present invention are described in the following by means of exemplifying embodiments.

It is noted that the present invention relates to all possible combinations of features recited in the claims. Further features of, and advantages with, the present invention will become apparent when studying the appended claims and the following description. Those skilled in the art realize that different features of the present invention can be combined to create embodiments other than those described in the following.

BRIEF DESCRIPTION OF THE DRAWINGS

Exemplifying embodiments of the invention will be described below with reference to the accompanying drawings, in which.

In the accompanying drawings, the same reference numerals denote the same or similar elements throughout the views.

DETAILED DESCRIPTION OF THE EMBODIMENTS

The present invention will now be described more fully hereinafter with reference to the accompanying drawings, in which exemplifying embodiments of the present invention are shown. The present invention may, however, be embodied in many different forms and should not be construed as limited to the embodiments set forth herein; rather, these embodiments are provided by way of example so that this disclosure will convey the scope of the invention to those skilled in the art. Furthermore, like numbers refer to like or similar elements or components throughout.

Figure 1:
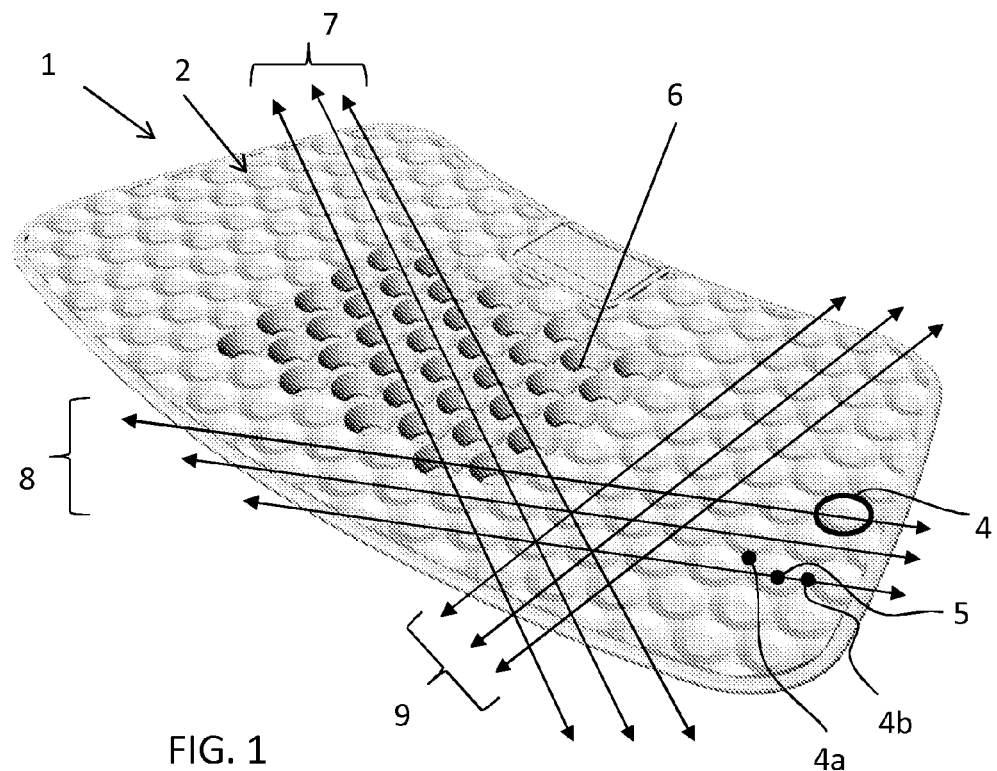
FIG. 1 is an elevated view of a first embodiment of the invention.

Referring now to FIG. 1, a first embodiment of the invention is disclosed. A light-emitting device 1 comprises a flexible pad 2 comprising a three-dimensional structure as shown on the drawing. The structure comprises a regular pattern of geometric features, in this case circular features. The circles are arranged according to a closed packed scheme. The perimeter 4 of the circular features is protruding from the plane of the paper. The surface area of the circles is recessed into the plane of the paper to provide recesses 5. In the center of the flexible pad 2, the circular recesses are replaced by conical apertures 6 engaging with light-emitting elements 16 from a light-emitting module 17 at the back of the flexible pad (shown in FIG. 2) such as for example LEDs mounted on an electronic textile. The area of the flexible pad comprising the apertures 6 is referred to as the light-emitting area 31 (shown in FIG. 2), which in FIG. 1 is surrounded with an area comprising recesses 5 referred to as the blind area 32 (shown in FIG. 2).

Figure 2:
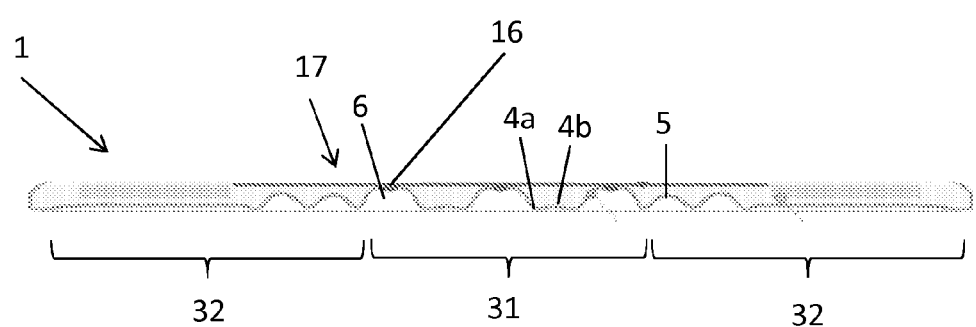
FIG. 2 is a cross section of an embodiment of the invention.
Figure 4:
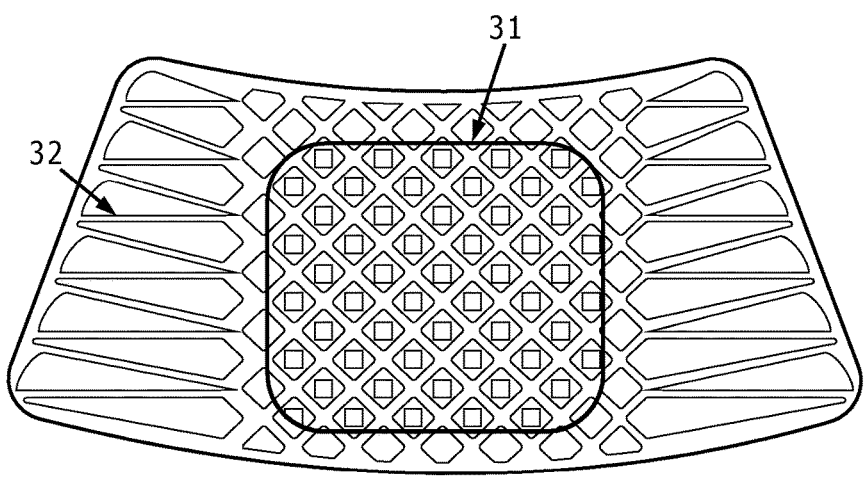
FIG. 4 is an elevated view of a third embodiment of the invention.

Now, also with reference to FIG. 2, which is a cross section of another embodiment of the invention, e.g. an embodiment comprising circular features 4 and 5 as shown in FIG. 1 with triangular features as shown as 32 of FIG. 4, the circular protrusions 4 may comprise extended parts 4a and withdrawn parts 4*b*, although the size of the drawing may not clearly show the height difference between extended and withdrawn parts of the circular protrusions 4. With reference to FIG. 1 the extended parts 4*a* of the circular protrusions 4 are provided where three adjacent circles meet and the withdrawn parts 4*b* of the circular protrusions 4 are provided where two adjacent circles meet. The withdrawn parts 4*b* line up in the direction of the lines 7, 8 and 9 shown in FIG. 1. In these directions, the recesses 5 and withdrawn parts 4*b* of the circular protrusions line up in an alternating way. As both the recesses 5 and the withdrawn parts 4*b* of the circular protrusions are recessed with respect to the extended parts 4*a* of the protrusions, which contact the skin when the light-emitting device 1 is applied to the skin, the alteration of recesses 5 and withdrawn parts 4*b* creates a open channel for ventilation and moisture evacuation when the device is applied to the skin. In a configuration as illustrated in FIG. 1 ventilation channels would be created in three directions 7, 8 and 9.

Figure 3:
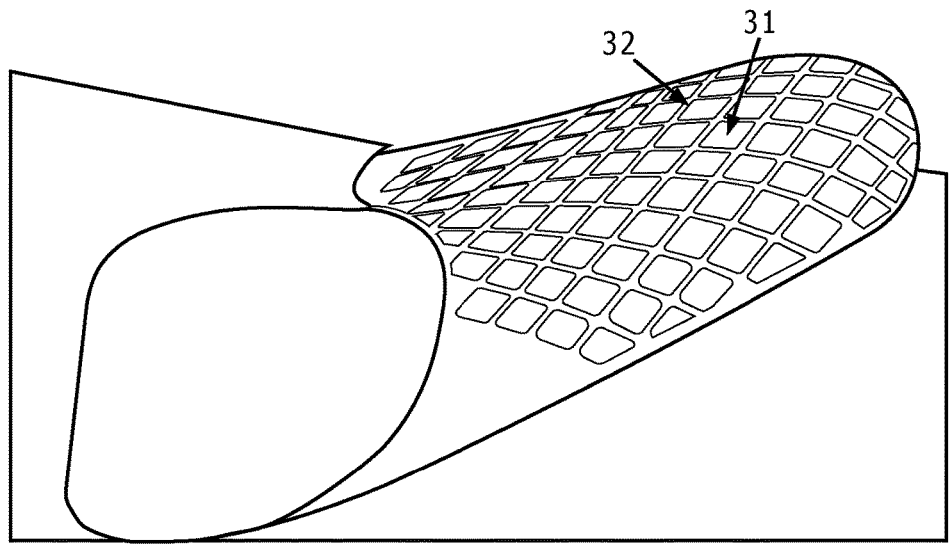
FIG. 3 is an elevated view of a second embodiment of the invention.

FIG. 3 shows another embodiment of the invention wherein the flexible pad is provided with a three-dimensional structure comprising a regular pattern of protruding features wherein these protruding features are based on regular hexagons. In this embodiment the angular points of the hexagons are extended and the line segments of the hexagons are withdrawn. As with the above described embodiment, the flexible pad comprises a light-emitting area 31 and a blind area 32 surrounding the light-emitting area.

FIG. 4 shows still another embodiment of the invention wherein the pattern of protrusions is different in the light-emitting area 31 and the surrounding blind area 32. As shown, in the light-emitting area 31 a pattern of rhombuses is used to build the protruding features, which also allows a dense packing of light-emitting elements. In the blind area 32 long stretched triangular features are used as protrusions which results in proportionally more recessed area versus protruding area.

While the figures illustrate protruding features based on geometric figures, it is clear that for example the angular points of the hexagons in FIG. 3 can also be realized as singular protruding points in a single recessed surface.

Concluding, a light-emitting device is disclosed. The light-emitting device comprises a flexible pad for position and conforming the light-emitting device to a portion of the body, wherein the flexible pad further comprises a three-dimensional structure having a plurality of protrusions for contacting the skin when the light-emitting device is applied to the skin, a plurality of recesses for creating a clearance between the skin and the flexible pad when the light-emitting device is applied to the skin, and a plurality of apertures for engaging with a plurality of light-emitting elements.

While the present invention has been illustrated and described in detail in the appended drawings and the foregoing description, such illustration and description are to be considered illustrative or exemplifying and not restrictive; the present invention is not limited to the disclosed embodiments. Other variations to the disclosed embodiments can be understood and effected by those skilled in the art in practicing the claimed invention, from a study of the drawings, the disclosure, and the appended claims. The mere fact that certain measures are recited in mutually different dependent claims does not indicate that a combination of these measured cannot be used to advantage. Any reference signs in the claims should not be construed as limiting the scope.

The invention claimed is:

1. A light-emitting device comprising:
    a light-emitting module comprising a plurality of light-emitting elements; and
    a flexible pad for positioning and conforming the light-emitting device to a portion of a body of a user, wherein the flexible pad comprises a three-dimensional structure, the three-dimensional structure including:
        a plurality of protrusions for contacting a skin of the portion of the body when the light-emitting device is applied to the skin, the plurality of protrusion defining a skin reference plane,
        a plurality of recesses for creating a clearance between the skin and the flexible pad when the light-emitting device is applied to the skin, and
        a plurality of apertures for engaging with the plurality of light-emitting elements,
        wherein each protrusion from the plurality of protrusions maps to a perimeter of a geometric figure, and
        wherein each protrusion comprises at least one extended part and at least one withdrawn part, wherein the at least one extended part is further extended than the at least one withdrawn part, wherein the at least one extended part contacts the skin when the light-emitting device is applied to the skin, and wherein a height difference exists between the plurality of recesses and the at least one withdrawn part of each protrusion.

2. The light-emitting device according to claim 1, wherein the at least one withdrawn part of each protrusion lines up with the plurality of recesses in at least one direction parallel with the skin reference plane of the flexible pad for creating a clearance channel in said at least one direction between the flexible pad and the skin when the light-emitting device is applied to the skin.

3. The light-emitting device according to claim 1, wherein the at least one extended part of each of the plurality of protrusions maps to one of an angular point of a polygon structure, a line segment of a polygon and an arc of a circle.

4. The light-emitting device according to claim 1, wherein the geometric figure is arranged in a regular pattern and is a close packing of one of polygons, circles, and hexagons.

5. The light-emitting device according to claim 1, wherein a height difference between the plurality of recesses and the plurality of protrusions, in a direction perpendicular to the skin reference plane of the flexible pad, is at least 0.5 mm.

6. The light-emitting device according to claim 1, wherein a width of a protrusion of the plurality of protrusions in a direction parallel with the skin reference plane of the flexible pad is less than 50% of a width of a recess of the plurality of recesses.

7. The light-emitting device according to claim 1, wherein a width of a recess of the plurality of recesses in a direction parallel with the skin reference plane of the flexible pad is between 5 mm and 20 mm.

8. The light-emitting device according to claim 1, wherein the three-dimensional structure comprises one of a woven structure and a foam structure.

9. The light-emitting device according to claim 1, wherein the three-dimensional structure comprises a water repellent and cleanable surface.

10. The light-emitting device according to claim 1, where the plurality of light-emitting elements emit light in one of a wavelength range from 430 nm to 460 nm, and a wavelength of 453 nm.

11. The light-emitting device according to claim 1, wherein the flexible pad further comprises an illumination area and a dark area, wherein the illumination area comprises at least a part of the plurality of apertures and the dark area comprises at least a part of the plurality of recesses.

12. The light-emitting device according to claim 11, wherein the plurality of protrusions is arranged in a regular pattern extending across the illumination area and the dark area.

13. The light-emitting device according to claim 11, wherein a size of the dark area is one of at least half a size of the illumination area, and at least a same size of the illumination area.

14. The light-emitting device according to claim 1, wherein a height difference between the plurality of recesses and the plurality of protrusions, in a direction perpendicular to the skin reference plane of the flexible pad, is 1.5 mm.

15. The light-emitting device according to claim 1, wherein a width of a protrusion of the plurality of protrusions in a direction parallel with the skin reference plane of the flexible pad is less than 20% of a width of a recess of the plurality of recesses.

16. The light-emitting device according to claim 1, wherein a width of a protrusion of the plurality of protrusions in a direction parallel with the skin reference plane of the flexible pad is less than 10% of a width of a recess of the plurality of recesses.

17. The light-emitting device according to claim 1, wherein a width of a recess of the plurality of recesses in a direction parallel with the skin reference plane of the flexible pad is between 10 mm and 15 mm.

18. The light-emitting device according to claim 1, where the plurality of light-emitting elements emit light in a wavelength of 453 nm.

19. A wearable, conformable phototherapy device including a light-emitting device, wherein the light-emitting device comprises:
    a light-emitting module comprising a plurality of light-emitting elements; and
    a flexible pad for positioning and conforming the light-emitting device to a portion of a body of a user, wherein the flexible pad comprises a three-dimensional structure, the three-dimensional structure including:
        a plurality of protrusions for contacting a skin of the portion of the body when the light-emitting device is applied to the skin, the plurality of protrusion defining a skin reference plane,
        a plurality of recesses for creating a clearance between the skin and the flexible pad when the light-emitting device is applied to the skin, and
        a plurality of apertures for engaging with the plurality of light-emitting elements,
        wherein each protrusion comprises at least one extended part and at least one withdrawn part, wherein the at least one extended part is further extended than the at least one withdrawn part, wherein the at least one extended part contacts the skin when the light-emitting device is applied to the skin, and wherein a height difference exists between the plurality of recesses and the at least one withdrawn part of each protrusion.

* * * * *